United States Patent
Melz et al.

(10) Patent No.: US 9,442,053 B2
(45) Date of Patent: Sep. 13, 2016

(54) TEST SAMPLE FRAME AND SYSTEM FOR DYNAMICALLY AND/OR CYCLICALLY LOAD TESTING A SAMPLE

(71) Applicant: Fraunhofer-Gesellschaft zur Foerderung der angewandten Forschung e.V., Munich (DE)

(72) Inventors: Tobias Melz, Darmstadt (DE); Michael Matthias, Weiterstadt (DE); Holger Hanselka, Darmstadt (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/417,634

(22) PCT Filed: Jul. 23, 2013

(86) PCT No.: PCT/EP2013/002193
§ 371 (c)(1),
(2) Date: Jan. 27, 2015

(87) PCT Pub. No.: WO2014/015980
PCT Pub. Date: Jan. 30, 2014

(65) Prior Publication Data
US 2015/0219538 A1    Aug. 6, 2015

(30) Foreign Application Priority Data

Jul. 27, 2012  (DE) .................. 10 2012 014 893

(51) Int. Cl.
*G01N 3/32* (2006.01)
*G01N 3/02* (2006.01)
*G01N 3/38* (2006.01)

(52) U.S. Cl.
CPC *G01N 3/02* (2013.01); *G01N 3/32* (2013.01); *G01N 3/38* (2013.01);

(Continued)

(58) Field of Classification Search
CPC ............ G01N 3/02; G01N 3/32; G01N 3/38; G01N 2203/0005; G01N 2203/0073; G01N 2203/0051; G01N 2203/0016; G01N 2203/0641; G01N 2203/0623; G01N 11/16; G01N 2203/0094; G01N 2203/0008; G01N 2203/0035; G01N 2203/0066; G01N 2203/0226; G01N 2203/0023; G01N 2203/0064; G01N 2203/0441
USPC ......... 73/808, 856, 649, 794, 797, 811, 855, 73/860, 857, 83
See application file for complete search history.

(56) References Cited

U.S. PATENT DOCUMENTS 4,491,759 A    1/1985  Kunz et al.
5,095,757 A *  3/1992  Larsen .................. G01N 3/04
                                                          73/857

(Continued)

FOREIGN PATENT DOCUMENTS

DE        2939923 C2    10/1981
DE        3309068 A      9/1984

(Continued)

*Primary Examiner* — Andre Allen
*Assistant Examiner* — Brandi Hopkins
(74) *Attorney, Agent, or Firm* — Fitch, Even, Tabin & Flannery LLP (57) ABSTRACT

The invention relates to a test system for dynamically and/or cyclically load testing a material sample, a component, or an assembly, hereinafter referred to as sample. The test system is provided with a test frame, to which a bearing and a counter bearing are attached. At least one actuator comprising a multifunctional solid state transducer material system is connected to the counter bearing, directly or indirectly, to which, also directly or indirectly, a fastener provides firm fixation of the sample. Likewise, on the bearing side, a fastener firm fixation of the sample such that the at least one actuator is able to introduce dynamic and/or cyclical mechanical loads into the sample, which act along a load path extending lengthwise between the bearing and the counter bearing and through the sample.

23 Claims, 3 Drawing Sheets (52) U.S. Cl.
CPC ............ *G01N 2203/0005* (2013.01); *G01N 2203/0016* (2013.01); *G01N 2203/0051* (2013.01); *G01N 2203/0073* (2013.01); *G01N 2203/0641* (2013.01)

(56) References Cited

U.S. PATENT DOCUMENTS

| | | | |
|---|---|---|---|
| 5,719,339 A | | 2/1998 | Hartman et al. |
| 5,959,215 A | | 9/1999 | Ono et al. |
| 6,023,980 A | * | 2/2000 | Owen .................. G01N 3/38 73/797 |
| 6,058,784 A | * | 5/2000 | Carroll .................. G01N 3/10 73/831 |
| 6,813,960 B1 | | 11/2004 | Owen et al. |
| 2002/0017144 A1 | | 2/2002 | Miles et al. |
| 2012/0318065 A1 | | 12/2012 | Neviere et al. |

FOREIGN PATENT DOCUMENTS

| | | |
|---|---|---|
| DE | 10204258 A1 | 4/2003 |
| DE | 102007038479 A1 | 2/2009 |
| WO | 2011/062322 A1 | 5/2011 |
| WO | 2011/086254 A1 | 7/2011 |

\* cited by examiner

TEST SAMPLE FRAME AND SYSTEM FOR DYNAMICALLY AND/OR CYCLICALLY LOAD TESTING A SAMPLE

CROSS REFERENCE TO RELATED APPLICATION

Reference is made to German Patent Application Serial No. 11/03.112, filed Oct. 12, 2011, which application is incorporated herein by reference in its entirety.

BACKGROUND OF THE INVENTION

1. Field of the Invention

The invention relates to a test system for dynamically and/or cyclically load testing a material sample, a component or an assembly, referred to in the following as the sample. The test system comprises a test frame to which a bearing and a counter bearing are attached. At least one actuator having a multifunctional solid state transducer material system is connected to the counter bearing, directly or indirectly, to which actuator, also directly or indirectly, a fastening means is attached for one-sided detachable, firm fixation of the sample. Likewise on the bearing side, a fastening means for one-sided detachable, firm fixation of the sample is provided such that the at least one actuator is able to introduce dynamic and/or cyclical mechanical loads into the sample, which act along a load path extending lengthwise between the bearing and the counter bearing and through the sample.

2. Description of the Prior Art

For the experimental investigation of the mechanical dynamic load bearing capability of material samples, components or assemblies having multiple components, test systems of the type described above are used to apply compressive and/or tensile loads to a sample under investigation in a dynamic, cyclical sequence. During the cyclical load application, the sample undergoes a continuous fatiguing process, which after numerous cyclical stress applications, that is load reversals, results in material degradations and associated crack formation with accompanying failure of the material.

In general, all cyclically loaded samples have a limited number of reversals and the amplitude of stress that acts cyclically on the sample. The capacity of a sample to withstand stress and the service life of the sample may be qualified on the basis of a number of load reversals the sample is able to sustain before macroscopically detectable signs of fatigue occur. The following four load reversal ranges have become established with regard to qualifying the service life of samples: The term low-cycle fatigue (LCF) is used when a sample fails after about $10^3$ load reversals. A sample has high cycle fatigue (HCF) if signs of fatigue begin to appear in the sample after about $10^8$ load reversals. The next load reversal frequency category is defined for samples that have a "high durability", (very high fatigue=VHF) and are able to sustain up to $10^{10}$ load reversals without damage. However, there is still some disagreement whether in general true durability is indicated, or whether failure occurs also even with very low stress amplitudes in the case of very load reversal numbers. Materials are considered to fall in the category of "ultra-high cycle fatigue" if they are able to sustain more than $10^{10}$ load reversals without damage.

Performing dynamically cyclical sample fatigue tests in which samples are to be exposed to $10^6$ or more load reversals is constrained by the use of conventional testing techniques, such as those that rely on servohydraulic test actuators which is financially impractical, particularly with respect to temporally significant limits. It is therefore obvious that in order to perform extremely large numbers of load reversals in the order of $10^{10}$ to $10^{12}$, the sample under investigation must be subjected to a mechanical vibration excitation with frequencies of 1 kHz and higher in order to make it possible to detect changes in fatigue strength for such an extremely large number of load reversals during a relatively short experiment period. It is precisely this object that was pursued in a method described in German application DE 10 2007 038 479 A1 for assessing the fatigue behavior of a material in which a sample to be tested is caused to vibrate at frequencies≥5 kHz by cyclical mechanical excitation.

An actuator having a piezoelectric material, preferably in the form of a piezoelectric stack actuator such as is used to generate mechanical stresses in a sample in a material testing machine in document PS 29 39 923 C2 is suitable for generating stress vibrations with frequencies of a few kHz that act in targeted manner on a sample. The test frame is constructed as a column-type test stand and comprises a counterweight supported on a foundation via elastic elements, on which the test frame, having a vertical strut and an upper crossbeam, is braced. The lower end of a material sample to be examined is clamped on one side directly to the lower counterweight via a counter bearing. The upper end of the material sample is enclosed by a bearing mounted on a vibration mass that is permanently attached to a piezoelectric stack actuator via an oscillating spring. The actuator is rigidly mounted on the crossbeam of the test frame. Since piezoelectric actuators are only able to produce small travel paths for vibrational excitation, the excitation frequency of the stack actuator is selected such that it matches the natural frequency of the vibrating spring-mass system of the material sample, the vibration mass, the oscillating spring and the test frame, so that the low excitation forces originating from the piezoelectric actuator are able to generate large inertia forces, which are taken up accordingly by the sample. Besides the "resonance mode", the known material test machine enables the sample to be examined in a "follow-on mode", that is, the material sample may be tested under desired stresses relative to forces with any predetermined test frequencies by a direct connection to the piezoelectric stack actuator via suitable connecting elements of the sample.

It is true that since its first use, a sensor system in a state of continuous technological evolution for detecting material degradations caused by the progressive material fatigue during the load reversal test has enabled physically detectable measurement parameters, for example oscillation amplitude, number of vibrations, acceleration forces acting on the sample, degradation effects on the sample surface, such as crack formation, etc. to be measured with ever increasing accuracy. But at the same time equally undesirable disturbances are also measured in the same way with equal accuracy, and these distort the measurement results.

Consequently, the conclusion is reached that cyclical stress tests of samples using conventional test machines with typically designed test frames, in the manner of a column test stand at test frequencies of >100 Hz are prone to significant error effects. As a result the quality of the overall test result may at least be cast into doubt. Particularly when testing modern samples and materials, which are intended, for example, to enable reliable lightweight construction for long-term and continuous use, it is essential to use reliable, highly dynamic testing techniques. Such test techniques, with which at least $10^8$ load reversal cycles are to be achieved, require test frequencies of at least several hundred Hertz, preferably 1 kHz and more. In particular, it is important to ensure that at such high test frequencies no critical vibration excitations are permitted to occur inside or outside the test device. Thus, it is important to prevent any undesirable resonant oscillations in the test system, in the sample being tested, and in structures close to the test system. It is also imperative to completely decouple the test system from its environment in a vibration-relevant manner.

An apparatus for conducting fatigue tests on a sample is disclosed in U.S. Published Application 2002/0017144 A1, in which a sample clamped at both ends is subjected to slow tensile or compressive alternating loads in the lengthwise direction, which are generated via an electromechanical spindle drive, a motor or a servohydraulic drive unit. At the same time, the sample is subjected to rapid alternating bending stresses provided by a piezoelectric actuator that acts on a fastening means and in a direction transversely to the tensile or compressive alternating loads. Excitation takes place at the resonance frequency of the sample until cracks appear and the sample breaks. U.S. Pat. No. 6,023,980 discloses a fatigue test device for high load cycle numbers with which vibration frequencies between 1 and 4 kHz can be produced, corresponding to typical vibration frequencies to which for example turbine blades are exposed. The apparatus comprises an inner frame, having two plates, and four rods that connect the plates. The sample is subjected to a static load, and to a dynamic load by two piezoelectric actuators with one acting on each of the samples.

Patent No. WO 2011/086254 A1 (D3) describes a device for monitoring mechanical properties of a viscoelastic material, in this case particularly a solid rocket fuel, with regard to any aging that manifests itself as softening of the material, due to moisture, for example, or as hardening, due to crosslinking of the material, for example. For this purpose, a sample of the material is brought into contact with a vibration source via a plate. Vibration signals are captured by a sensor at the opposite end of the sample.

SUMMARY OF THE INVENTION

The invention improves a test system for dynamically and/or cyclically load testing a sample, comprising a test frame to which a bearing and a counter bearing are attached, at least one actuator having a multifunctional solid state transducer material system connected directly or indirectly to the counter bearing, a fastening means attached directly or indirectly to the actuator for one-sided detachable, firm fixation of the sample, and a fastening means attached directly or indirectly to the bearing for one-sided detachable, firm fixation of the sample such that the at least one actuator introduces dynamic and/or cyclical mechanical loads into the sample, which act along a load path extending lengthwise between the bearing and the counter bearing and through the sample to significantly reduce the interference influences on the sample that have a lasting effect on the test. In particular, measures are implemented which are designed to improve the quality of measurement results when testing samples with test frequencies>100 Hz, preferably of 1000 Hz. Measures to be carried out on the test system should be easy to implement in design engineering terms, and must not feature additions to the test system that are excessively heavy, of outsize dimensions or difficult to handle.

The inventive test system is characterized in that, in contrast to the conventional design having a column test stand, the inventive test stand comprises least two frame parts joined together into a capsular element, at least one first and one second frame part, of which the first frame part at least partially encases at least one actuator, and is connected to the at least one actuator by the counter bearing. The second frame part projects above the first frame part in a dome shape, and is provided with a recess oriented laterally to the load path, in which the bearing is mounted lengthwise with respect to the load path. Supports are attached to the capsular test frame to brace the frame, each of the supports resting on a bearing attached to a support structure.

The test frame that is joined together from the at least two frame parts to create a unitary, capsular body has a self-contained body structure that provides the test frame with structural rigidity that suppresses any and all vibrational excitations even in parts of the test frame, at least for the frequency- and amplitude-specific vibration area in which the actuator is excited and is designed to generate oscillations for the purpose of examining the sample.

The structural design of the test frame having the form of a capsule and the choice of material from which are made the at least two frame parts that combine to form the capsular test frame are tuned and carried out with respect to one another in such manner that a first resonance frequency assignable to the test frame is in a frequency range significantly higher than the working range of the actuator. This makes it impossible for any resonant structural vibrations originating from the test frame to be superimposed as interference on the load vibrations originating from the actuator, which act directly on the sample in the lengthwise direction of the load path.

The outer appearance of test frame designed according to the invention has a capsular or teardrop spatial shape. The term "capsular or teardrop spatial shape" is understood to be a characterization referring to the outer appearance of the test frame that is defined by an integral, continuous test frame surface that completely surrounds at least the sample and the actuator, with the exception of an opening allowing access to the sample, and which corresponds to the shape of a capsule surface, resembling the shape of an ellipsoid or a torpedo. The shape of the test frame substantially ensures that the load forces generated by the action of the actuator and exerted on the sample are disseminated and redistributed as evenly as possible inside the test frame, so that force-induced stress peaks or maxima occurring inside the test frame may be prevented to the extent possible. The test frame according to the invention thus advantageously uses the predetermined natural principle of intelligent load redistribution and a consequently enhances stability of a shell structure, as is observed in the natural shape of eggs or the pods of legumes.

The test frame is designed with a longitudinal extension that is expediently aligned vertically. To this end, braces are attached to the capsular test frame, each of which is preferably disposed in a center of gravity plane of the test frame, and is supported on a bearing mounted on a support structure. The support structure may be formed by a conventional construction of support struts, which supports the entire dead weight of the test system constructed according to the invention. The arrangement and bearing of the test system constructed according to the invention is advantageously equivalent to a spatially free bearing, in which the capsular test frame is supported on just two, preferably three or more supports attached laterally along the longitudinal extension thereof, each of which are supported by bearings mounted on the support structure. With the exception of supports, the capsule-shaped test frame has no contact with its surroundings, that is the test frame is almost entirely surrounded by air. Such a bearing also helps considerably to minimize, or almost completely suppress vibration excitations from the surrounding medium that might have an interfering effect on the test frame.

In order to achieve the inherent rigidity of the capsular test frame as described in the preceding and the additional requirement of a self-contained force flow inside the test frame, which is generated by the dynamic stress test of the sample by the at least one actuator, a test frame construction according to the invention described in a more detailed explanation is provided by the embodiment illustrated in the drawing.

BRIEF DESCRIPTION OF THE INVENTION

The invention will be described in the following without limitation of the general inventive thought on the basis of an exemplary embodiment thereof and with reference to the drawing. In the drawing.

DETAILED DESCRIPTION OF THE INVENTION

Figure 1:
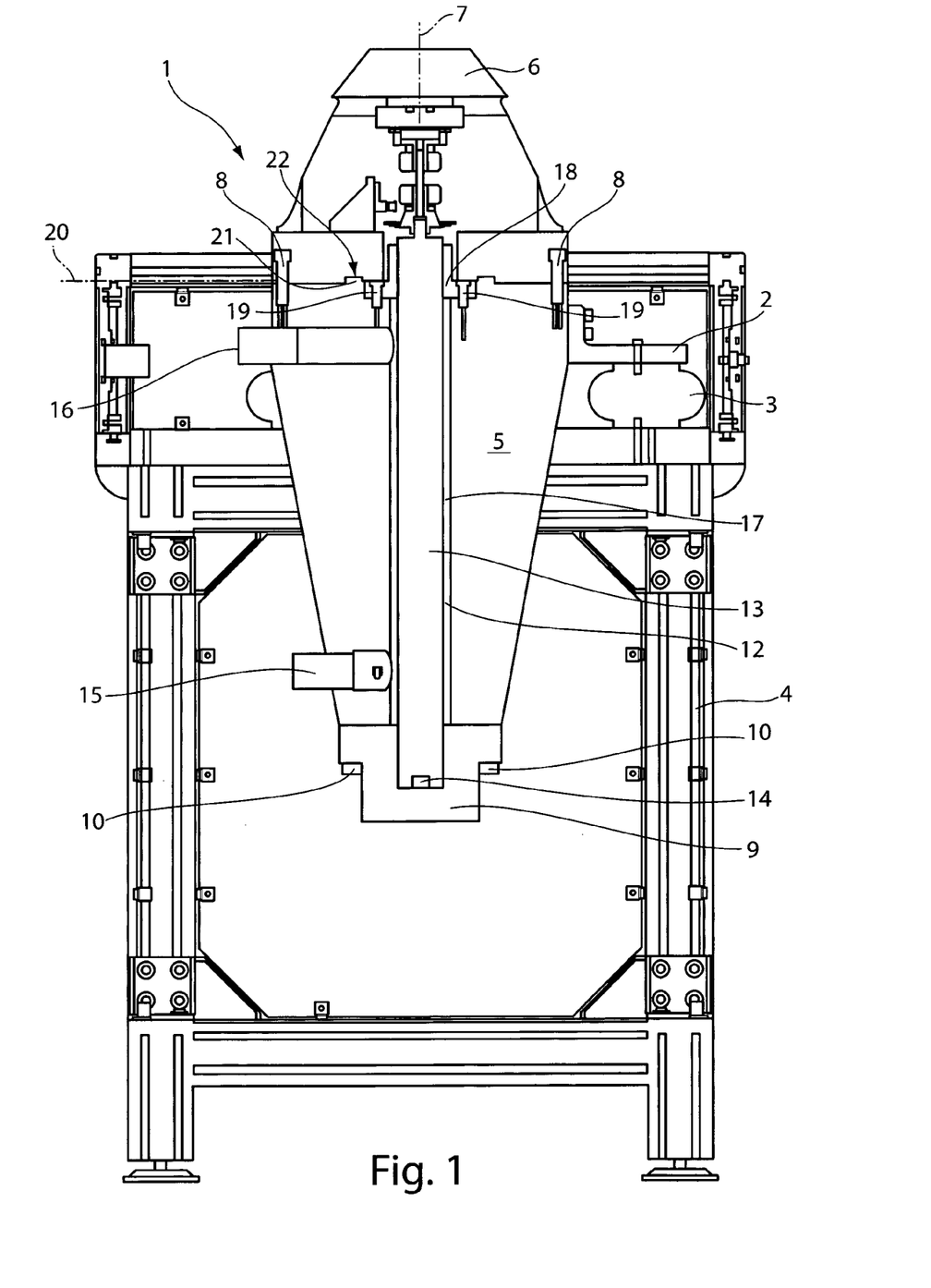
FIG. 1 shows a longitudinal section through a test system constructed according to the invention, mounted in a support structure.

FIG. 1 is a schematic, longitudinal sectional view through the test system designed according to the invention, including a test frame 1 constructed in the form of a capsule, which rests on a supporting structure 4 via a support 2 attached laterally to test frame 1 via elastic bearings 3.

Capsular test frame 1 is constructed from two frame parts which are a first frame part 5 and a second frame part 6.

Capsular test frame 1, assembled from the two frame parts 5 and 6, has a longitudinal axis 7 of the capsule frame that is oriented vertically by virtue of the sole bearing of test frame 1 via support 2 on support structure 4. Because of the vertical orientation of the longitudinal axis of the capsule, second frame part 6 is positioned above first frame part 5, wherein the upper, second frame part 6 has an outer contour that is flared in a dome-shape vertically downward in the longitudinal extension thereof. In the region of the largest cross section thereof, second frame part 6 lies flush against the first, lower frame part 5. Both frame parts 5 and 6 are releasably fixed, preferably joined to each other by screw connections 8. The second frame part 6 advantageously has a longitudinal extension to the longitudinal axis of the capsule that corresponds to not more than ⅓ of the longitudinal extension of the body of the entire test frame 1.

Figure 3:
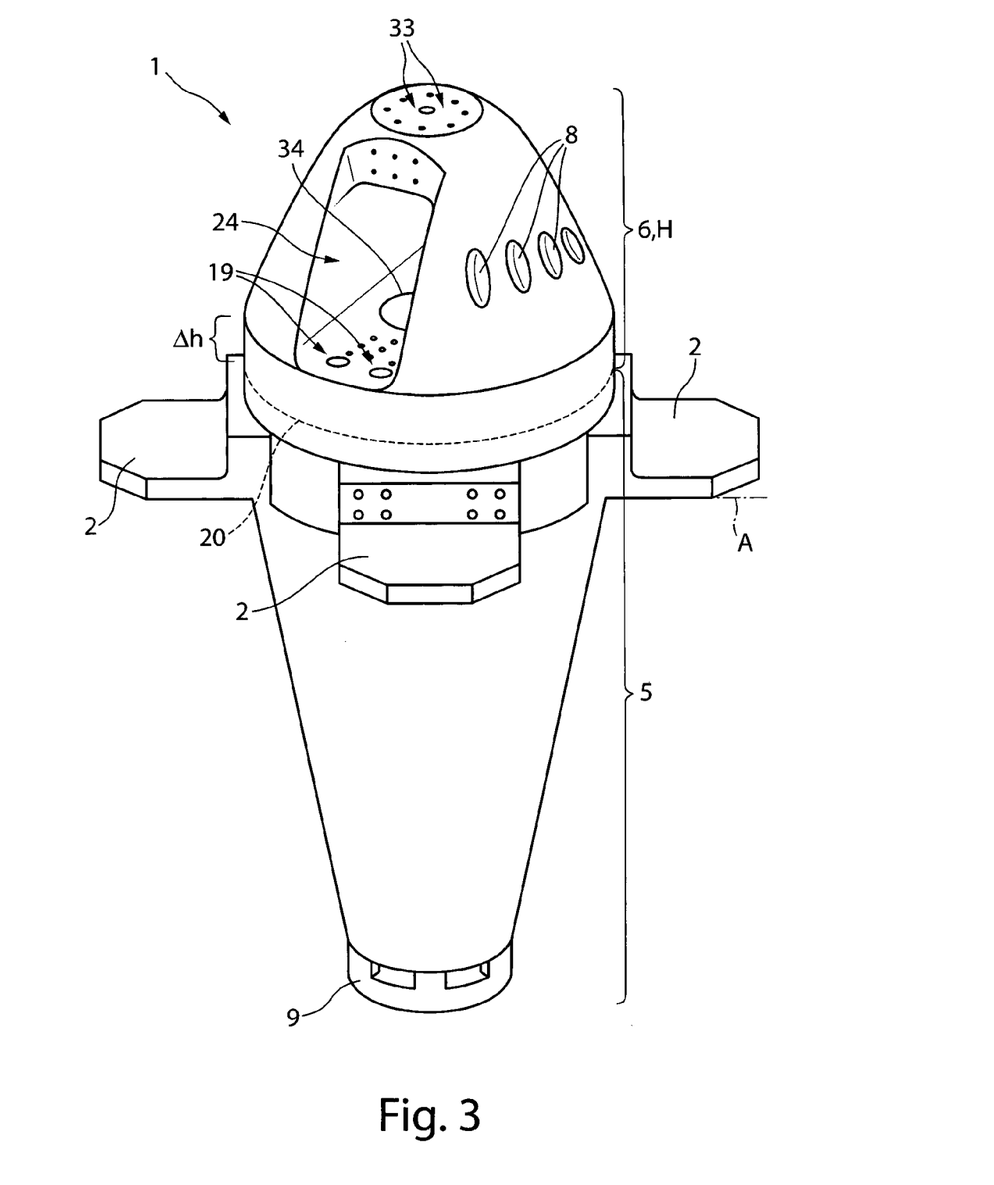
FIG. 3 is a perspective view of the test frame.

The first frame part 5 has an outer contour, as shown in FIG. 3, with a cross section that is tapered vertically downwardly in the longitudinal extension thereof. The cross section of first frame part 5 is preferably tapered conically downwards.

In the embodiment as shown, lower, first frame part 5 is terminated with an end cap 9 which is inserted in lower, first frame part 5 in releasably secure manner, with screw connections 10. It is also possible to produce the lower, first frame part 5 as a one-part component, with end cap 9 being integral with the rest of frame part 5.

From the longitudinal sectional view, the test frame 1 which is shaped as a capsule or teardrop to optimize forced flow distribution inside the frame.

The first frame part 5 also has a hollow channel 12 in the center of the longitudinal extension of the capsule. The channel 12 is preferably formed by a fluid-tight joint between first frame part 5 and end cap 9 with a blind hole. An actuator 13, which is an elongated rod-shaped stack actuator of piezoelectric material, is fitted into hollow channel 12.

Actuator 13, which is described in the following as the piezoelectric actuator, is connected at the lower end thereof to a counter bearing 14, which is integrated in end cap 9. The upper end of piezoelectric actuator 13 protrudes out of first frame part 5 and fits into a region of second frame part 6, as will be explained in the following.

The first frame part 5 has a feed line 15 and a discharge line 16, each of which is in fluid communication with inner hollow channel 12. The cross-sectional dimensions of hollow channel 12, and of piezoelectric actuator 13 are matched with each other so that a circular annular space 17 is enclosed between piezoelectric actuator 13 and the inner wall of hollow channel 12, along which a cooling medium—in the form of a refrigerant or a gas-phase coolant, for example—can flow, with which piezoelectric actuator 13 comes into thermal contact. The suitably chosen cooling medium is fed into inner annular chamber 17 via feed line 15 and escapes to the outside via outlet 16. In order to prevent the cooling medium from escaping in an uncontrolled manner through the upper end of hollow channel 12, a sealing and longitudinal guide unit 18 is fitted inside hollow channel 12, and lies radially tightly and in fluid-tight manner about piezoelectric actuator 13, which protrudes above first frame part 5, without restricting the actuator in the movement thereof longitudinally to the longitudinal axis of the body 7. In the case shown, sealing and longitudinal guide unit 18 is also fastened detachably to first frame part 5 by screw connections 19.

Second frame part 6 rests above first frame part 5 and flush against first frame part 5 with respect to the outer contour and also relative to the common parting plane 20 between first and second frame parts 5 and 6. Screw connections 8 are used to produce a firm, detachable joining of second frame part 6 to first frame part 5, and rigidly connecting the second frame part 6 physically to first frame part 5. The connection between the two frame parts 5 and 6 is effected in such manner that the joint has the quality of a one-piece construction of first and second frame parts 5 and 6, so that in particular no relative movements can occur inside test frame 1, particularly with regard to a power flow created between the two frame parts 5 and 6. For the purpose of centering along the common longitudinal body axis 7 for the joining operation, as well as for purposes of a perfectly fitting joint and connection between the two frame parts 5 and 6 the first frame part 5 has an extension 21 the rises above parting plane 20 and fits into a corresponding recess 22 in second frame part 6.

The first and also the second frame part 5 and 6 are shaped so that the largest cross-section of the body of each is located in the region of common parting plane 20. Second frame part 6 has a dome-shaped outer contour, which is evident in FIGS. 1 and 2, and which has an extremely small body cross section perpendicularly intersecting the longitudinal axis 7 at the uppermost end of second frame part 6, and continuously flares downwards to form a dome or cone until the largest body cross-section thereof, which lies at least in parting plane 20.

Figure 2:
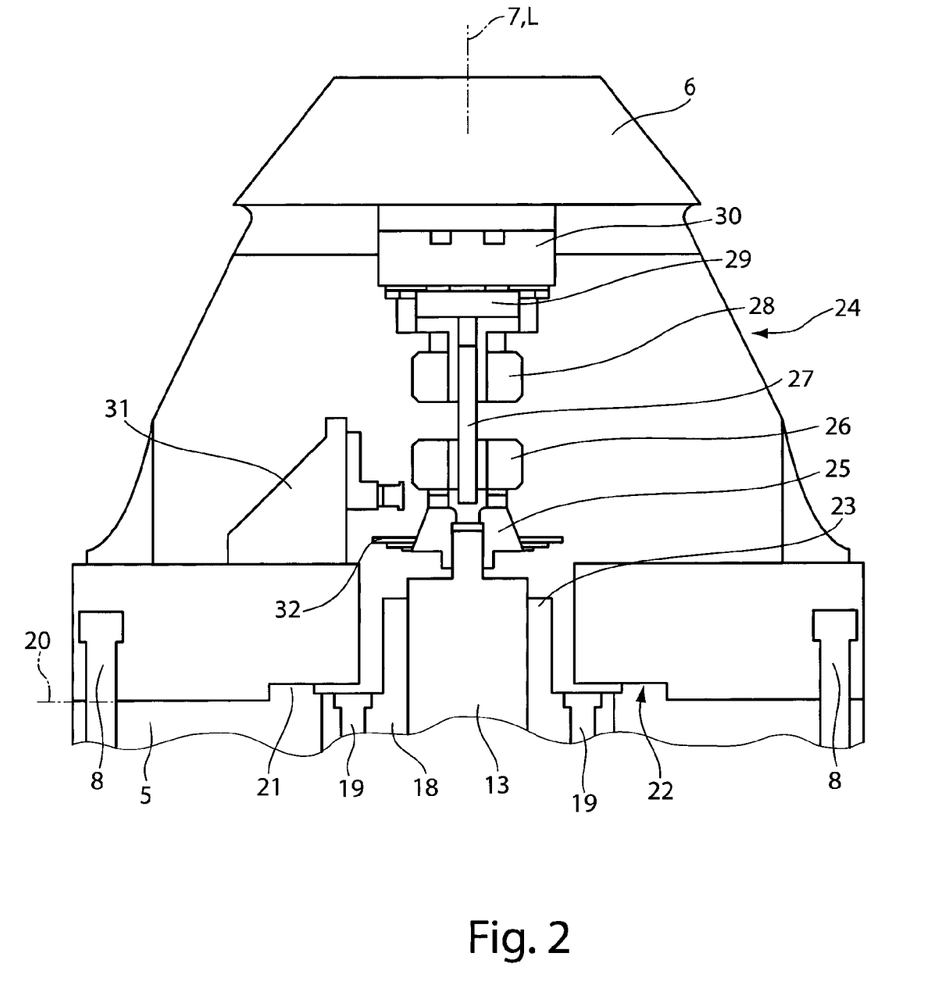
FIG. 2 shows an enlarged view of the upper test frame part.

For a further description of second frame part 6, and the components of test system 1 located therein, reference is made to the enlarged partial illustration according to FIG. 2.

In order to avoid repetition, the reference numerals already described are not described again in connection with FIG. 2. The upper part of piezoelectric actuator 13 extends above parting plane 20 and openly engages in a central recess 23 within second frame part 6. The central recess 23 is aligned coaxially with the longitudinal capsule axis 7, and preferably also with hollow channel 13.

The upper end of piezoelectric actuator 13 is releasably firmly connected to a connecting flange 25, which in turn is connected to a fastener 26, to which the lower end of sample 27 may be fastened in fixed manner. The upper end of sample 27 is also fixedly connected with a fastener 28, which is connected to a pressure load cell 29 longitudinally with load path L, which coincides with the longitudinal axis 7 of the capsule. Finally, pressure load cell 29 is fixedly connected to a bearing 30, which is mounted on the inner wall of the dome-shaped second frame part 6.

Optionally, another actuator (not shown) may be integrated along load path L, for example in the area of bearing 30, of connecting flange 25 and/or of counter bearing 14, via which a controllable force may be brought to bear on actuator 13. The additional force serves as a mechanical bias and/or a low-frequency cyclical test load acting on actuator 13. Hydraulic, pneumatic or electromechanical actuators have proven to be particularly suitable for use as such an additional actuator. Of course, another solid-state actuator such as a piezoelectric actuator is also suitable for use as an additional actuator.

For reasons of rigidity and stability, both the second frame part 6 and first frame part 5 are preferably made from a solid metal material. To ensure that sample 27 can easily be installed in the test system, the upper, second frame part 6 is furnished with a recess 24 that laterally passes completely through frame part 6, and along which the sample 27 may be inserted by hand in the correspondingly provided fasteners 26 and 28. Lateral recess 24 thus represents a cavity that is open on two sides within the otherwise solid construction of second frame part 6.

An optical position sensor 31 is also mounted inside second frame part 6 and detects the path deflection of piezoelectric actuator 13 with a light beam reflected by a mirror 32 that is attached to fastening flange 25.

FIG. 3 shows a perspective view of the capsule-shaped test frame 1, from which the three-dimensional shape of test frame 1 is discernible. The dome-shaped, upper frame part 6 is constructed as a solid body and has a circular cross-section aligned longitudinally along parting plane 20, on which the first and second frame parts 5 and 6 are joined to each other firmly but detachably by screw connections. Starting from parting plane 20, upper frame part 6 is initially cylindrical in shape, with a constant circular cross-section. After a distance $\Delta h$, as measured from parting plane 20, wherein $\Delta h \leq \frac{1}{4}$ of the total height H of second frame part 6, the outer contour of the second frame part becomes narrower with increasing distance from parting plane 20, preferably corresponding to a surface shape of a spheroid.

Recesses of the blind hole type are created inside second frame part 6, into which screw connections 8 and 19 may be inserted for purposes of securing second frame part 6 to first frame part 5, and which firmly but detachably fix second frame part 6 with respect to first frame part 5. In order to simplify the mounting of bearing 36 (see FIG. 2), the upper tip of second frame part 6 is flattened and has corresponding fastening apertures 33. In addition, a central, circular opening 34 is created in the area of the circular cross section of second frame part 6, which is characterized by distance $\Delta h$, through which opening actuator 13 protrudes upwards into the test chamber through the frontal face on one side, and which is defined by lateral recess 24, which passes completely through second frame part 6 transversely to the longitudinal direction thereof.

First lower frame part 5 is aligned flush with the upper part of the second frame 6 at parting plane 20 with the same circular diameter and also comprises a section with constant circular diameter directed downwards from parting plane 20. In this area, there are four supports 2, arranged at regular intervals about the circumference of circularly shaped first frame part 5, by which the entire dead weight of test frame 1 is braced against a support structure 4, which is illustrated in FIG. 1.

Subsequently downwards in the direction of support plane A defined by the four supports 2, the first frame part 5 also tapers conically and is terminated at the bottom end thereof by an end cap 9 (not shown in FIG. 3), which is also attached firmly but detachably by screw connections.

FIG. 3 shows that the capsular or torpedo-like conformation of test frame 1 has a substantially rotationally symmetrical three-dimensional shape, which is only interrupted by the laterally completely continuous recess 24, through which may be inserted all components mounted inside second frame part 6 for supporting and measuring a sample 27.

The system illustrated in FIGS. 1 to 3 is characterized according to the invention by the shape of test frame 1, which is constructed in the form of a capsule of a teardrop, or similar to a torpedo shape, which has good physical rigidity, such that no structural vibrations of any kind that might be initiated by piezoelectric actuator 13 occur inside the test frame, at least in a frequency range that is of significance for the test. Due to the physical configuration of test frame 1, the actuator-generated forces are guided inside test frame 1 in the manner of a self-contained force flow that has no local force flow maxima that might lead to local structural vibrations. With the exception of the recesses that locally pass through the first and second frame parts, and the lateral recess 24 in the upper, second frame part 6 and the feed and drain 15, 16 in the lower, first frame part 5, frame 1 is also rotationally symmetrical. Both frame parts 5 and 6 are joined at the common parting plane 20 and in the area of extension 21 and recess 22, respectively along an annular surface, in a force fit, due to screw connectors 8.

Capsular test frame 1 is mounted on support structure 4 via elastic bearings 3, which are capable of suppressing both possible oscillations on the part of test frame 1 on support structure 4, and in the reverse direction of the force flow exerted by support structure 4 on test frame 1.

The test system according to the invention enables precise coupling of actuator-generated oscillations in a sample that is to be exposed to load inversion cycle number of up to $10^{12}$. This is assured with a piezoactuator, which is typically able to generate oscillation frequencies of 1 kHz and higher. Because of the design specifications and the choice of material, any structural natural frequencies that occur within the test frame are significantly higher than the oscillation frequency of the actuator, so that resonant structural excitations in the test frame can be precluded.

LIST OF REFERENCE NUMERALS

1 Test frame
2 Support
3 Bearing
4 Support structure
5 First frame part

6 Second frame part
7 Longitudinal body axis
8 Screw connector
9 End cap, closure element
10 Screw connector
12 Hollow channel
13 Piezoelectric actuator
14 Counter bearing
15 Feed
16 Discharge
17 Annular cavity
18 Sealing and longitudinal guide unit
19 Screw connector
20 Parting plane
21 Extension
22 Recess
23 Recess
24 Lateral recess
25 Connecting flange
26 Fastener
27 Sample
28 Fastener
29 Pressure load cell
30 Bearing
31 Displacement sensor
32 Mirror
33 Mounting aperture
L Load path
A Support plane

The invention claimed is:

1. A test system for dynamically and/or cyclically load testing a sample, comprising:
a test frame to which a bearing and a counter bearing are attached, the test frame including at least one actuator including a solid state transducer material system coupled to the counter bearing, a fastener coupled to the at least one actuator for holding one end of the sample and for holding another end of the sample which is coupled to the bearing so that the at least one actuator introduces dynamic and/or cyclical mechanical loads into the sample, which act along a load path extending longitudinally between the bearing and the counter bearing through the sample; and wherein
the test frame comprises at least a first and second frame part joined together detachably to form a capsule, the first frame part at least partially encasing the at least one actuator and is connected to the at least one actuator by the counter bearing and the second frame part projects above the first frame part, has a dome and is provided with at least one recess oriented laterally to the load path in which the bearing is mounted longitudinally with respect to the load path; and
supports are attached to the test frame with each support on a bearing attached to a support structure; and
wherein the capsule has a longitudinal axis which is vertically oriented, in at least a longitudinal section through the capsule, the second frame part has a vertically flared outer contour defining the dome, the first frame part has an outer contour with a cross-section tapering vertically downwardly in the longitudinal direction and the second frame part is aligned flush with the first frame part in an area of the largest cross-section of the capsule.

2. A test system according to claim 1, wherein:
the supports are arranged in plane at the center of gravity of the test frame.

3. A test system according to claim 2, wherein:
the downwardly tapering cross-section is conical.

4. A test system according to claim 3, wherein:
the second frame part extends longitudinally and has a length not more than ⅓ of a length of the capsule.

5. A test system according to claim 2, wherein:
the second frame part extends longitudinally and has a length not more than ⅓ of a length of the capsule.

6. A test system according to claim 2, wherein:
the at least first and the at least second frame parts comprise a solid metal material or fiber-reinforced plastic.

7. A test system according to claim 1, wherein:
the downwardly tapering cross-section is conical.

8. A test system according to claim 7, wherein:
the second frame part extends longitudinally and has a length not more than ⅓ of a length of the capsule.

9. A test system according to claim 7, wherein:
the at least first and the at least second frame parts comprise a solid metal material or fiber-reinforced plastic.

10. A test system according to claim 7, wherein:
the first frame part comprises a hollow channel running centrically along the body longitudinal axis and the channel includes either a blind hole or a channel passing completely through the first frame part which is closeable to be fluid tight at the lower end thereof by a closure element; and
the actuator is located inside the hollow channel and is fixed at one side to the counter bearing mounted at a bottom end of the blind hole or the closure element and the upper end of the actuator engages at a lateral recess to the second frame part.

11. A test system according to claim 1, wherein:
the second frame part extends longitudinally and has a length not more than ⅓ of a length of the capsule.

12. A test system according to claim 11, wherein:
the at least first and the at least second frame parts comprise a solid metal material or fiber-reinforced plastic.

13. A test system according to claim 11, wherein:
the first frame part comprises a hollow channel running centrically along the body longitudinal axis and the channel includes either a blind hole or a channel passing completely through the first frame part which is closeable to be fluid tight at the lower end thereof by a closure element; and
the actuator is located inside the hollow channel and is fixed at one side to the counter bearing mounted at a bottom end of the blind hole or the closure element and the upper end of the actuator engages at a lateral recess to the second frame part.

14. A test system according to claim 1, wherein:
the at least first and the at least second frame parts comprise a solid metal material or fiber-reinforced plastic.

15. A test system according to claim 1, wherein:
the first frame part comprises a hollow channel running centrically along the body longitudinal axis and the channel includes either a blind hole or a channel passing completely through the first frame part which is closeable to be fluid tight at the lower end thereof by a closure element; and
the actuator is located inside the hollow channel and is fixed at one side to the counter bearing mounted at a bottom end of the blind hole or the closure element and the upper end of the actuator engages at a lateral recess to the second frame part.

16. A test system according to claim 15, comprising:

a longitudinal seal and guide disposed in an upper part of the channel conforming to a circumferential edge of the at least one actuator and defining an annular space surrounding the at least one actuator within the hollow channel which is fluid tight; and at least two connections and a fluid flow path extending through the first frame part and communicating with the annual space through which a cooling medium is fed into and transported out of the annular space through the connections.

17. A test system according to claim 16, comprising:

a longitudinal seal and guide disposed in an upper part of the channel conforming to a circumferential edge of the at least one actuator and defining an annular space surrounding the at least one actuator within the hollow channel which is fluid tight; and at least two connections and a fluid flow path extending through the first frame part and communicating with the annular space through which a cooling medium is fed into and transported out of the annular space through the connections.

18. A test system according to claim 16, wherein:

an upper end of the at least one actuator is connected to the fastener to fix one side of the material sample and other end of the material sample is connected coupled via the other fastener to the bearing which is mounted at an area of the second frame part which straddles the lateral recess.

19. A test system according to claim 15, wherein:

an upper end of the at least one actuator is connected to the fastener to fix one side of the material sample and other end of the material sample is connected coupled via the other fastener to the bearing which is mounted at an area of the second frame part which straddles the lateral recess.

20. A test system according to claim 1, comprising:

an eddy current sensor which detects deflection of the material sample and a pressure load cell for measuring force along the load path in the area of the bearing.

21. A test system according to claim 1, wherein:

the test frame contains forced flow caused by dynamic load testing of the material sample by the at least one actuator.

22. A test system according to claim 1, comprising:

the at least one actuator is disposed along the load path through which static and/or dynamic forces are exerted on the at least one actuator.

23. A test system according to claim 22, wherein:

the at least one further actuator comprises a hydraulic, pneumatic or an electromechanical actuator.

* * * * *